(12) United States Patent
Nygren et al.

(10) Patent No.: US 6,267,964 B1
(45) Date of Patent: *Jul. 31, 2001

(54) STABILIZED PROTEIN OR PEPTIDE CONJUGATES ABLE TO BOND ALBUMIN HAVING EXTENDED BIOLOGICAL HALF-LIVES

(75) Inventors: Per Åke Nygren, Enskede; Hans Wigzell, Hägersten; Mathias Uhlén, Kvarnbogatan, all of (SE)

(73) Assignee: Affibody Technology Sweden AB, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/162,906

(22) Filed: Dec. 8, 1993

Related U.S. Application Data

(63) Continuation of application No. 07/828,819, filed on Mar. 3, 1992.

(30) Foreign Application Priority Data

Aug. 1, 1989 (SE) .................................... 8902638
Jul. 31, 1990 (WO) .................................. PCT/SE90/00509

(51) Int. Cl.⁷ ............................ A61K 39/00; C12N 15/62
(52) U.S. Cl. ................................ 424/197.11; 424/192.1; 424/193.1; 424/195.11; 435/69.7; 530/350; 536/23.4; 536/23.5; 536/23.7
(58) Field of Search ..................... 530/350, 402, 530/825; 435/69.7; 935/10; 424/192.1–197.11

(56) References Cited

U.S. PATENT DOCUMENTS

| | | | |
|---|---|---|---|
| 4,703,039 | 10/1987 | Hawiger et al. | 514/21 |
| 5,082,773 | * 1/1992 | Fahnestock | 435/69.1 |
| 5,100,788 | * 3/1992 | Löfdahl et al. | 435/69.7 |
| 5,116,964 | * 5/1992 | Capon et al. | 536/27 |

FOREIGN PATENT DOCUMENTS

| | | |
|---|---|---|
| 0 136 835 | 4/1985 | (EP) . |
| 0 317 641 | 5/1989 | (EP) . |
| 0 314 317 B1 | 8/1998 | (EP) . |
| WO 89/05140 | 6/1989 | (WO) . |

OTHER PUBLICATIONS

P.A. Nygren et al. J. Mol. Recognet 1(2):69–74 Apr. 1988 (Abstract Only Enclosed).*
M. Uhlen et al., J. Biological Chemistry 259(3):1695–1702, 1984.*
B. Jansson et al., Protein Engineering 2(6):555–561, 1989.*
M.I. Johnston et al. Science 260:1286 May 28, 1993.*
E. Gilboa et al. Trends in Genetics 10(4):139–144 Apr. 1994.*
Proc. Natl. Acad. Sci. USA, vol. 86, pp. 4367 to 4371, Jun. 1989 "Dual affinity fusion approach and its use to express recombinant human insulin–like growth factor II", Björn Hammarberg et al.
Dialog Information Services, File 155: Medline 66–90/Nov., Accession No. 06820435, T. Ogino et al. "Chemical Modification of Superoxide Dismutase. Extension of Plasma Half–Life of the Enzyme Through the Reversible Binding to the Circulating Album", Int. J. Pept. Protein Res., 32(2), pp. 153–159, Aug. 1988.

* cited by examiner

Primary Examiner—Lorraine Spector
(74) Attorney, Agent, or Firm—Burns, Doane, Swecker & Mathis, L.L.P.

(57) ABSTRACT

A process for extending the half-life in vivo by a biologically active protein or peptide, characterized by covalently coupling said protein or peptide to a polypeptide fragment capable of binding to a serum protein, whereby when administering the resulting protein or peptide conjugate its binding to the serum protein results in extended biological activity, the use of the protein or peptide conjugate above for manufacturing a medicament which, when administered to a mammal including man, shows extended half-life in vivo; and a method of therapeutic or prophylactic treatment.

9 Claims, 4 Drawing Sheets

STABILIZED PROTEIN OR PEPTIDE CONJUGATES ABLE TO BOND ALBUMIN HAVING EXTENDED BIOLOGICAL HALF-LIVES

This application is a continuation of application Ser. No. 07/828,819, filed Mar. 3, 1992.

The present invention relates to the use of biologically active proteins or peptides in the form of products showing improved stability in vivo, i.e. extended half-life, and the invention relates inter alia to the use of recombinant vectors capable of replication in a host cell to produce such useful products. More specifically, the invention relates to a protein or peptide conjugate capable of selective binding to a host protein or macromolecule, thus stabilizing the biologically active protein or peptide in this host. The invention also extends to a process for extending the half life in vivo of a biologically active protein or peptide and to the use of a protein or peptide conjugate resulting from such process for the manufacture of a medicament.

Although the present invention in the following will be mainly illustrated through protein or peptide conjugates produced by recombinant DNA technology the invention is not limited to such production system but is equally useful when such protein or peptide conjugate is prepared by chemical covalent coupling of its constituents.

Gene fusion is a procedure wherein the coding sequence of two or more genes are spliced together to form a combined gene which on expression in a suitable host organism will produce a fusion product wherein the separate proteins or polypeptides coded for by the respective genes are fused together into a single molecule.

The rapid depletion of bioactive proteins in vivo is, in some cases, a limiting factor for the efficiency of therapeutic compounds. Examples of products of potential clinical interest with short half-lives in vivo are components such as soluble human CD4, having an interest in the treatment of AIDS, which have a half-life in rabbit of 15 minutes (Watanabe et al., Nature, 337, 1984, 267–270) and human t-PA used in the treatment of blood clots with a halflife of only 2–3 minutes in humans (Hollander, Critical Reviews in Biotechn. 6, 1987, 253–271). Such short half-lives of therapeutically interesting proteins might make it necessary to distribute the compound to the patient either with a high initial dose or with many repeated distributions in order to keep the level of the compound at a clinically relevant level. This reduces the cost effectiveness of the drug and might cause negative side-effects due to the high doses necessary.

To overcome these problems several systems for slow release of drugs have been designed, in which the therapeutic agent is encapsulated by physical means to release the drug in a delayed manner (i.e. entero or depot tablets) or is delivered as a pro drug, inactive until chemically modified within the patient. In this way, it is in some cases possible to prolong the action of the therapeutic agent, although the actual in vivo half-life of the compound in circulation has not increased.

Recently, an alternative strategy has been described using fusions between a recombinant protein and a host protein such as IgG (Capon et al., Nature 337, 1989, 525–531) or IgM (Karjalainen et al., Nature 339 (1989) 68–70). In this way, the half-life of recombinant soluble CD4 in vivo was shown to be substantially prolonged. However, this strategy of distributing therapeutically interesting compounds have the disadvantage that unwanted immunological reactions are possible and that the half-life of the thus produced recombinant fusion protein might not be substantially prolonged.

Also for the development of vaccines and other immunostimulatory preparations, a rapid depletion of the antigen from the circulation might decrease the immune response. In order to present the antigen to the immune system in an efficient manner different vehicles have been developed, thereby increasing the immune response. (Allison et al. Journ. of Imm. Methods, 95 (1986), 157–168).

This strategy is often accompanied by simultaneous injection with weakened or killed pathogens such as in Freund's complete adjuvant (FCA). However, these formula have the potential risk of being toxic to the recipient and might lead to denaturation of the protein, thus limiting the use of this strategy for the distribution of therapeutic proteins.

The present invention provides new improved means to facilitate the stabilization of proteins and polypeptide products in vivo. According to the present invention this is achieved by coupling, such as by fusion of the desired biologically active protein or polypeptide to a binding-protein capable of selective binding to a host protein or macromolecule thus stabilizing the desired protein in said host. By selective binding to a patient protein with a relatively long half-life, the depletion of the fusion protein is retarded. By the term "patient" used in the present disclosure is intended a living animal, especially a mammal including man.

In accordance with a preferred aspect of the present invention, gene fusion is used to combine a first DNA-sequence coding for a binding protein with a second DNA-sequence coding for a desired protein or polypeptide into a functional gene capable of expressing the fusion product of said desired binding protein part.

Due to the binding ability the produced protein or polypeptide is stabilized in vivo in the receptor host.

Accordingly, the present invention is based on the surprising finding that the half-life in vivo of a biologically active protein or peptide can be substantially prolonged by covalently coupling such protein or peptide to a polypeptide fragment capable of binding to a serum protein. This finding was totally unexpected and could not be predicted from available scientific knowledge.

Thus, according to one aspect of the invention, there is provided a process for extending the half-life in vivo of a biologically active protein or peptide, such process comprising the steps of covalently coupling the protein or peptide to a polypeptide fragment which is capable of binding to a serum protein. When administering the protein or peptide conjugate resulting from such process the binding thereof to the serum protein results in substantially extended biological activity due to increased half-life thereof.

According to a preferred embodiment of this aspect of the invention said polypeptide fragment is capable of binding to serum albumin, such as a serum albumin of mammal origin, for example human serum albumin.

The binding polypeptide fragment of the conjugate preferably originates from streptococcal protein G.

Another aspect of the invention is constituted by the use of the protein or peptide conjugate as defined above for the manufacture of a dug or medicament which, when administered to a mammal including man, shows extended half life in vivo thus prolonging the biological activity of the conjugate.

A preferred aspect of the present invention is thus the provision of a recombinant DNA cloning vehicle or vector comprising a DNA sequence coding for a desired protein or polypeptide operatively linked to a DNA sequence coding for a binding mediating part, such that said DNA-sequences together code for a fusion protein of said desired protein or polypeptide, said binding mediating part being capable of selectively binding to a protein or macromolecule present in the patient to be treated.

By transforming a compatible host organism with said vector to permit expression of the above combined DNA sequence and culturing the host organism in a nutrient medium the corresponding binding mediating fusion protein or polypeptide will be produced. Host cells producing functional fusion proteins should be used, which could be bacterial cells, such as Escherichia or eukaryotic cells, such as fungi, insect cells, plant or mammalian cell cultures. The transformation of the hosts may be effected with well-known methods.

Said fusion protein of said desired protein or polypeptide and said binding mediating protein produced by the cultured host organism can be efficiently isolated from the cell culture by means of standard protein purification methods such as size exclusion chromatography, ion exchange chromatography or affinity purification using a suitable ligand immobilized to a suitable carrier.

if the fusion product is secreted into the surrounding medium the purification may be initiated directly from the medium. If, on the other hand, the fusion product remains within the cells the later have to be ruptured before such purification can be effected. Rupture of the cell walls may be effected in a conventional manner by, e.g., high pressure, ultrasonication, homogenization, shaking with glass-beads etc. In cases where the product is trapped within the periplasmic space between two cell membranes, as in gram negative bacteria, an osmotic shock procedure may be used to release the product into the suspension medium. Any other treatment of the cultured cells or the growth medium prior to the isolation of the fusion product is, of course, also within the scope of the invention.

In a conventional manner the fusion protein in solution is injected in vivo into the recipient. Due to the part which mediates binding to a patient protein or macromolecule, the stability of the desired protein or polypeptide is increased.

Alternatively, formation of complexes between said fusion protein and the appropriate patient protein or macromolecule can be accomplished in vitro, whereafter the said complexes are injected into the recipient.

The methods for preparing solution of said fusion protein for injection are well-known and need not be described in any detail herein.

The conditions suitable for in vitro complex formation should, of course, be chosen with regard to the particular binding mediating protein and desired protein or polypeptide involved.

An example of such part which mediates specific binding to a patient protein is the albumin binding regions of streptococcal protein G. (Nygren et al., Journ. of Mol. Recogn. 1, (1988), 69–74). Serum albumin with a half-life in humans of 19 days is the most abundant protein in the serum (40 g/l) and one of its functions is to bind molecules such as lipids and bilirubin. (T. Peters Jr., Advances in Protein Chemistry, 37 (1985) 161–245).

As the albumin-binding regions of streptococcal protein G, designated A1B1A2B2A3, or parts thereof, have a highly specific binding to serum albumin (Nygren et al., Journ. of Molec. Recogn. 1 (1988) 69–74) it is conceived that this protein could be used to construct recombinant fusion proteins, which bind to serum albumin and are carried around in the patient with a distribution resembling serum albumin.

Other examples of parts mediating specific binding to host proteins or macromolecules are receptors, such as the IgG-binding regions of staphylococcal protein A (Uhlen et al., J. Biol. Chem. 259, 1695–1702 (1984)) or streptococcal protein G (Guss et al. EMBO. J. 5, 1567–1575 (1986)) or the staphylococcal fibronectin receptor (Kuusela R., Nature 276, 718–720 (1978)).

One valuable use of such a fusion product is when the protein fused to the part mediating binding to patient proteins or macromolecules has a therapeutic function. In such cases a prolonged in vivo half-life of the desired protein or polypeptide is essential for its clinical use. Examples of such therapeutic proteins or polypeptides are soluble CD4-receptors for AIDS/HIV-treatment, tissue plasminogen activator (tPA) for dissolving blood clots present in the recipient who is injected and hormones used for growth stimulation (hGH, IGF-I, IGF-II, TNF, EGF) or any other clinically relevant function (i.e. insulin, relaxin).

Another valuable use of the invention is for the production of monoclonal and polyclonal antibodies.

According to the invention a recombinant protein, to which one wants to obtain antibodies, is fused to a binding protein to prolong the half-life in circulation in vivo of said recombinant protein. The longer half-life provides a longer exposure to the immune system and thus will give higher titers than conventional methods.

Yet another valuable use of the invention is in the production of vaccines. Recombinant proteins used in vaccines can thus be stabilized in vivo, which can make adjuvants superfluous and in general give higher immunological response.

As appears from the above a crucial part of the present invention is the provision of the recombinant DNA structure or vector comprising the combined gene coding for the present fusion protein or polypeptide and capable of transforming a host cell to permit expression thereof and production of the fusion product. The present invention is intended to encompass any such vector irrespective of how it has been obtained using, for example, various restriction enzyme cutting, ligating, transforming and screening techniques well-known in the art as well as any appropriate vector materials and host-organisms. Thus, the DNA sequence coding for the desired protein or polypeptide may be inserted into a suitable vector and the binding coding DNA sequence inserted subsequently, or vice versa: or the two DNA sequences may be introduced simultaneously into the vector. It is also possible to insert the respective DNA sequences in parts thereof into the vector. Further the two DNA sequences may be arranged with either the binding coding sequence or the sequence coding for the desired protein or polypeptide at the 5'-end or start of the combined gene. The special techniques for accomplishing such insertions and combinations with maintained correct reading frames, including the provision of suitable restriction sites therefore, are well-known per se in the art.

The invention also covers a recombinant DNA molecule comprising the recombinant DNA sequence as described above and fused at the 3' end thereof at the DNA level of a production gene. By this arrangement such molecule obtains the ability to express a fused protein in a suitable host.

Finally, the invention covers a plasmid vector comprising the recombinant DNA molecule as described above. The invention also extends to bacterial or eukaryotic cells harboring the recombinant DNA molecule defined above. The molecule can be inserted in the chromosome of the cell but may also be contained in a autonomously replicating vector, such as plasmid, phage or virus.

The invention will in the following be further illustrated by non-limiting examples with reference to the appended drawings wherein:

FIG. 1 is a schematic drawing of the streptococcal protein G gene (as described by Olsson et al. in Eur. J. of Biochem. 168, pp 318–324) and the constructs containing fragments thereof. For comparison is also shown the construct encoding the Z protein. In row A: pEZT; row B: pB2T, row C: the protein G gene and in row D: pBBCD4;

FIG. 2 shows the levels of label remaining in the blood circulation during an 18-day period in Maqaque monkeys injected with $^{125}$I-labelled proteins B2 and Z. Values are relative to levels observed 20 minutes post injection;

FIG. 3 shows in lane 1 and lane 2 an analysis of SDS-PAGE of HSA-affinity purified proteins from the culture medium of E. coli cells harboring pBBCD4 (material in lane 2 is diluted 10 times relative to lane 1.) Lane M: marker proteins with molecular weights as indicated.

STARTING MATERIALS

Figure 1:
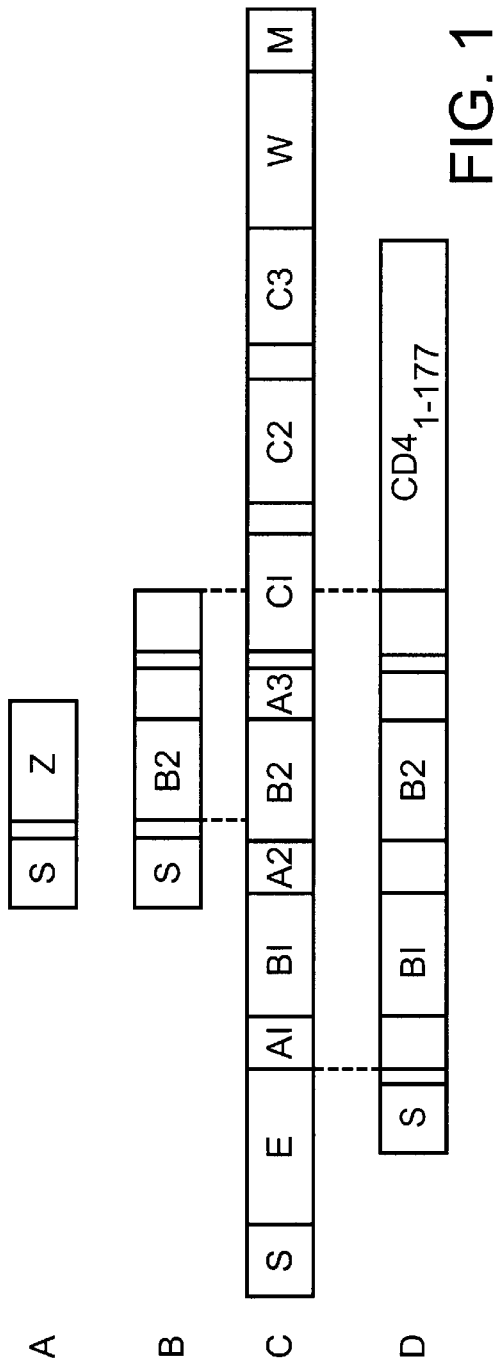

E. coli strain RR1ΔM15 (Langley et al. Proc. Natl. Acad. of Sci., USA, 72, 1254–1257 (1975)) was used in the examples. The cloning vehicles used were:

pEZZT308 (Nygren et al., J. of Molec. Recogn. 1, 69–74 (1988))

pEG (Eliasson et al., J. of Biol. Chem. 263, 4323–4327 (1988))

pUC418 (kindly provided by Dan R. Littman at University of California, San Francisco).

pB1B2 (Nygren et al., J. of Molec. Recogn. 1, 69–74 (1988)).

All the strains and vectors are available at the Dept. of Biochemistry, Royal Institute of Technology, Stockholm, Sweden.

Plasmid pNP-3 has ben deposited on Jun. 14, 1989 at Deutsche Sammlung von Mikroorganismen und Zellkulturen GmbH in Braunschweig, Germany, and given the accession number DSM 5394, in accordance with the Budapest Treaty.

Oligonucleotides:
NYPE-1:
5'-CGAATTCGCCTAACGGTATGCAGGGAAAC-AAAGTGGTGCTGGGC-3'
NYPE-2:
5'-CGGATCCAGGCATCACGATGTCTATTTTGAA-CTCGAGC-3' were custom made by KabiGen AB using solid phase technology.

PCR reactions were carried out on a Techne programmable Dri-Block PCH-1.

BUFFERS AND MEDIA

TSB: Tryptic Soy Broth, made up to one liter and autoclaved.

TST: TRIS/HCl (25 mM) pH 7.4, 150 mM NaCl, 0.05% Tween 80.

Osmotic Shock solution I: 20% sucrose, 0.3 M TRIS/HCl pH 8.1, 1 mM EDTA.

Osmotic Shock solution II: 5 mM MgCl$_2$ (0° C.).

SDS-PAGE loading buffer: 2.5% SDS (sodium dodecyl sulphate, 5% dithiothreitol (DTT), 0.01% Bromophenol blue.

10×PCP-buffer: 10 mM TRIS/HCl, pH 8.3, 5 mM KCl, 1.5 mM MgCl$_2$, 0.01% gelatin

PBS: 0.05 M Sodium phosphate pH 7.1, 0.9% NaCl.

PCR-AMPLIFICATION

An amplification mixture was prepared consisting of the template pUC418 (8 ng/μl), oligonucleotides NYPE-1 and NYPE-2 (each 0.2 μM), 1×PCR-buffer, dNTP's (each 0.2 mM) and 2 units of Taq-polymerase (Stratagene). The time/temp profile used was 92° C. (1 min), 50° C. (2 min) and 72° C. (1 min). This cycle was repeated 35 times.

PROTEIN LABELLING

After lyophilization proteins were resolved in distilled water to a concentration of 4 mg/ml. 100 μg (25 μl) protein, 50 μl of 0.2 M Na phosphate buffer (pH7.2), 50 μl Enzymobeads (BioRad Inc.) and 25 μl of 1% β-glucose was mixed with 1 mCi Na$^{125}$I (10 μl) and incubated for 20 min. The supernatant was subsequently loaded on a 5 ml G-25 Superfine Sephadex column (Pharmacia, Sweden) previously equilibrated with PBS (0.1% gelatin). Elution with the same buffer and collection in small fractions efficiently separated labelled proteins from free Na$^{125}$I.

AFFINITY PURIFICATION OF PROTEINS

Cells harboring the different constructs were grown overnight in Tryptic Soy Broth (TSB) supplemented with Ampicillin 70 mg/l. After centrifugation at 5000 g, the periplasmic content was released using an osmotic shock procedure according to Nossal and Heppel (J. of Biol. Chem. 244, 3049–3062) involving incubation first with 20% sucrose, 0.3 M TRIS/HCl pH 8.0, 1 mM EDTA followed by 0.5 mM MgCl$_2$ (0° C.). Shock lysates were loaded directly on IgG-Sepharose (Z) or HSA-Sepharose (B2) respectively. After washing with 1×TST (25 mM TRIS/HCl pH 7.4, 0.15 M NaCl, 0.05% Tween™ 80) followed by 0.5 mM NH$_4$Ac, pH 6.0, proteins were eluted with 0.5 M HAc, pH 2.8. The absorbtion at 280 nm was measured and relevant fractions were lyophilized.

DISTRIBUTION OF PROTEINS IN MAQAQUES

Four Maqacues in the range of 6–7 kg were injected with approximately 100 μg of labelled protein using a leg vein. At each sample collection 0.5 ml blood was withdrawn for further analysis. For all samples taken during the 18-day period, the actual measurement of radioactivity was performed on day 18, to eliminate errors due to the half-life of the isotope.

FRACTIONATED AMMONIUM SULPHATE PRECIPITATION

Precipitation with ammonium sulphate was performed using standard techniques at 40 and 70% of saturation on 150 μl plasma collected 24 hours after injection.

ROUTINE METHODS

Methods used routinely in molecular biology are not described (like the use of commercial restriction enzymes, DNA-ligations, Bal 31 exonuclease, S1 nuclease and Klenow polymerase, transformation of E. coli and isolation of plasmid DNA).

In order to analyze protein fractions by SDS-PAGE using the PHAST-system (Pharmacia, Uppsala, Sweden), the samples were dissolved in loading buffer [2.5% SDS, 5% Dithiothreitol (DTT) and 0.01% Bromphenol blue]. Gradient (8–25% polyacrylamide gels with 5% SDS were run at 10 mA for 30 min and subsequently stained with Coomassie-blue.

EXAMPLE 1

Plasmid pEZZT308 (Nygren et al., Journ. of Mol. Recogn. 1, 69–74 (1988)), encoding a synthetic divalent IgG-binding domain, ZZ, preceded by the transcription, translation and secretion signals of staphylococcal protein A (SPA), was digested with the restriction endonuclease BglII, thus releasing a 174 base pair fragment. After recovery from an agarose gel the vector part was religated to yield pEZT, encoding a single IgG-binding domain Z (FIG. 1).

Eliasson et al. (Journ. of Biol. Chem. 263, 4323–4327 (1988)) have described the construction of the plasmid pEG, encoding a protein consisting of the B2, A3, C1, D1 and C3-regions of streptococcal protein G, mediating binding to both IgG and HSA. In order to subclone a fragment encoding only a HSA-binding protein, plasmid pEG was digested with restriction endonucleases Not I and Pst I, releasing a 640 base pair fragment. This was ligated to the purified vector fragment of pEZZT308, previously digested with the same endonucleases. The resulting plasmid pB2T (FIG. 1) encodes a HSA binding protein designated B2 under the same control signals of SPA as above.

Overnight cultures of *E. coli* cells harboring the plasmid pEZT or pB2T were harvested using an osmotic shock procedure. The lysates were loaded directly on columns of IgG-(Z) or HSA-Sepharose (B2) for affinity chromatography. After lyophilization the purified proteins were resolved and $^{125}$I-labelled.

In total four Maqaque monkeys were intravenously injected with labelled proteins. Individuals #300 and 233 were given Z-protein and individuals #277 and 278 B-protein. Twenty four hours after injection the distribution of labelled protein within the plasma was analyzed by fractionated ammonium sulphate precipitation at 40% and 70% of saturation, respectively.

TABLE 1

| Individual | Protein | cpm.start | cpm.pellet 40% | cpm.pellet 70% |
|---|---|---|---|---|
| 300 | Z | 14833 | 11733 (79%) | 440 (3.0%) |
| 233 | Z | 8615 | 6069 (70%) | 426 (4.9%) |
| 277 | B | 17197 | 260 (1.5%) | 14273 (83%) |
| 278 | B | 22170 | 346 (1.6%) | 18242 (82%) |

As shown in Table 1, in serum originating from apes injected with Z-protein, the majority of label was found in the precipitate at 40% of saturation fraction. This finding was expected as at this level of saturation the precipitate mainly consists of the immunoglobulin content of the serum.

In contrast, in plasma from monkeys injected with B2-protein, the label was found to be located in the precipitate at 70% of saturation. At this level of saturation the precipitate mainly consists of serum albumin. These two results indicate that both recombinant proteins behave as expected in vivo as regarded to their respective affinity.

Furthermore the clearance of the two proteins in the apes was followed during an 18-day period. Twenty minutes after injection the amount of label present in the blood was determined as a reference value. The levels of label remaining in the blood during the period was compared to this initial value.

Figure 2:
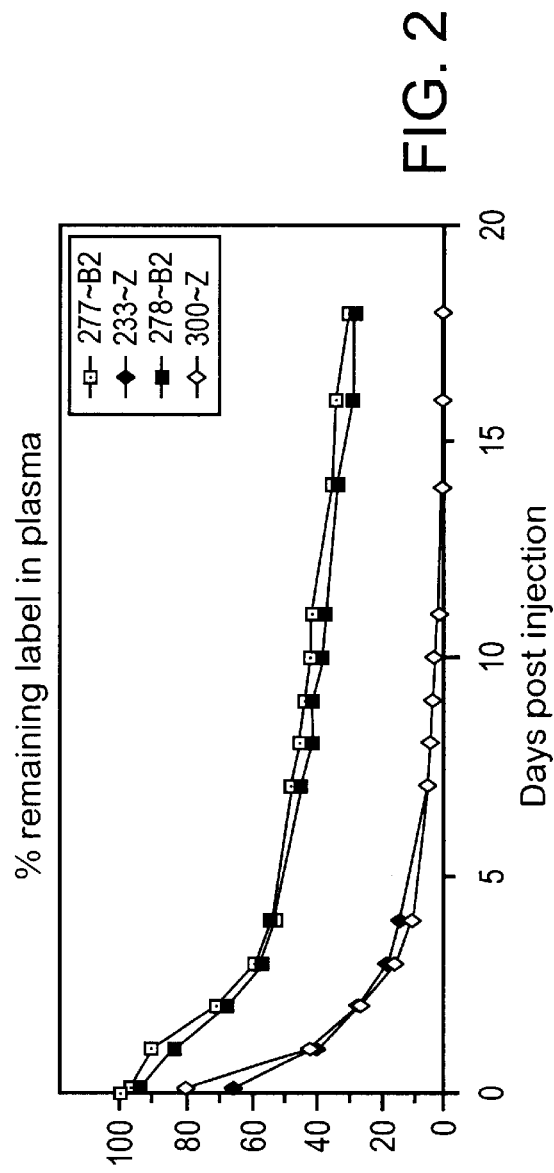

As can be seen in FIG. 2, the levels of label in both apes injected with Z-protein is rapidly decreasing, approaching 10% already after 6 days. This effective clearance might in part be explained by immunological responses to complexes formed between Z-protein and IgG.

Interestingly, in apes injected with B2-protein, the levels of labelled protein present in the blood remains high during the entire 18-day period. After an initial decrease, probably due to a distribution of B2/HSA complexes to the extravascular albumin pool, the levels remaining in both apes resemble the expected decline as regards to the turnover of an average HSA-molecule with a half-life in humans of 19 days. (T. Peters Jr., Advances in Protein Chemistry, 37, 161–245 (1985)).

EXAMPLE 2

Plasmid pB1B2 was digested with restriction enzymes EcoRI and SalI, treated with Klenow polymerase and religated to yield pB1B2 ΔR/S. A synthetic oligonucleotide (5'-TGCAAGATCTTTCAATTTCCCTATCCTCGAGA-ATTCTAAGCTT-3' and its complementary sequence) was inserted in pB1B2 ΔR/S previously cleaved with PstI and HindIII, giving rise to plasmid pB1B2HIV resistant to PstI. A multipurpose cloning linker derived from M13mp18 was cloned between the EcoRI and HindIII restriction sites, resulting in expression of the LacZ' gene positioned immediately downstream. The resulting plasmid was designated pB1B2HIVmp18.

A region encoding amino-acids 1–177 of the mature human CD4 T-cell receptor was in vitro amplified from plasmid pUC418 using the oligonucleotides NYPE-1 and NYPE-2 as primers for the polymerase chain reaction (PCR). After digestion with restriction enzymes EcoRI and BamHI the fragment was ligated into the multilinker of pB1B2HIVmp18 encoding the serum albumin binding domains of streptococcal protein G. The resulting plasmid designated pNP-3 thus encodes a fusion protein consisting of said serum albumin binding region and domains E1 and E2 of the human CD4 molecule involved in the binding to glycoprotein gp120 of HIV-1 (Bedinger et al., Nature 334 (1988) 162–164).

Figure 3:
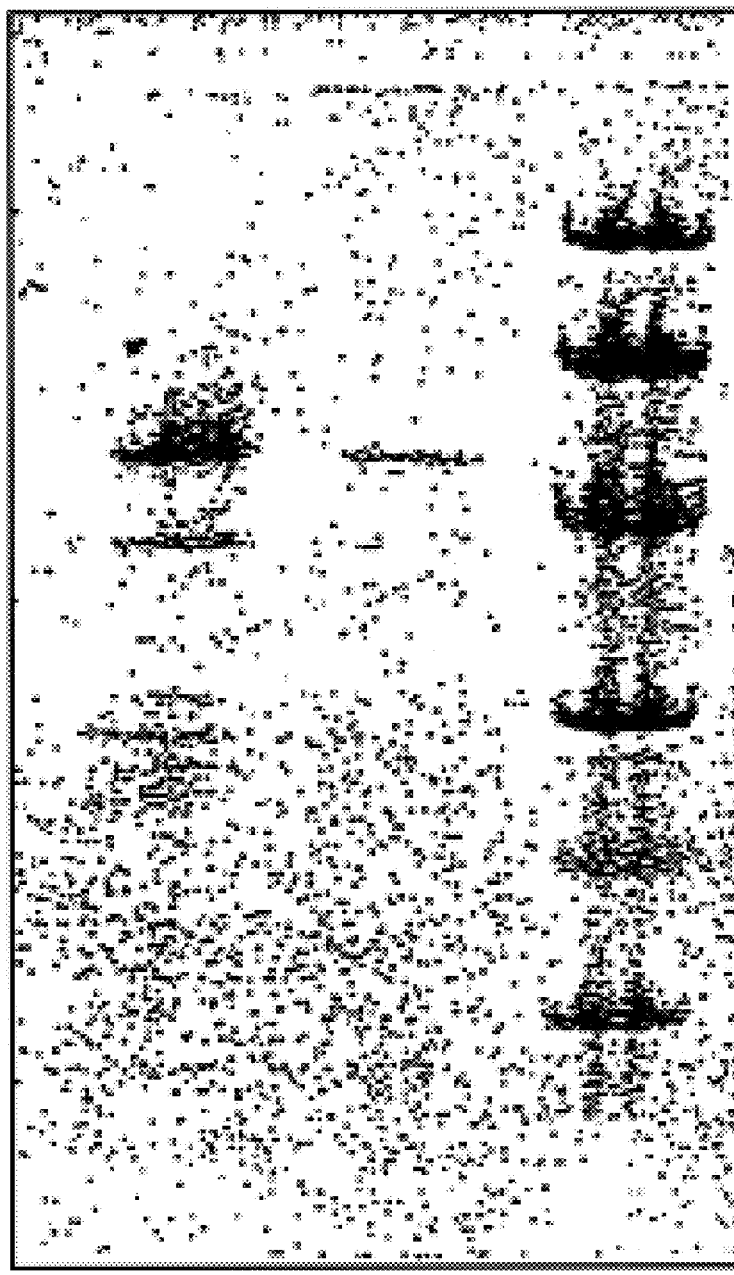

*E. coli* RR1ΔM15 cells harboring plasmid pNP-3 were cultivated at 30° C. over night. Analysis on SDS-PAGE on proteins from culture medium affinity purified on HSA-Sepharose shows that the fusion protein is stable in the host and has an apparent molecular weight of 48 kDa (FIG. 3) which is in accordance with estimations from the deduced amino acid sequence.

EXAMPLE 3

Figure 4:
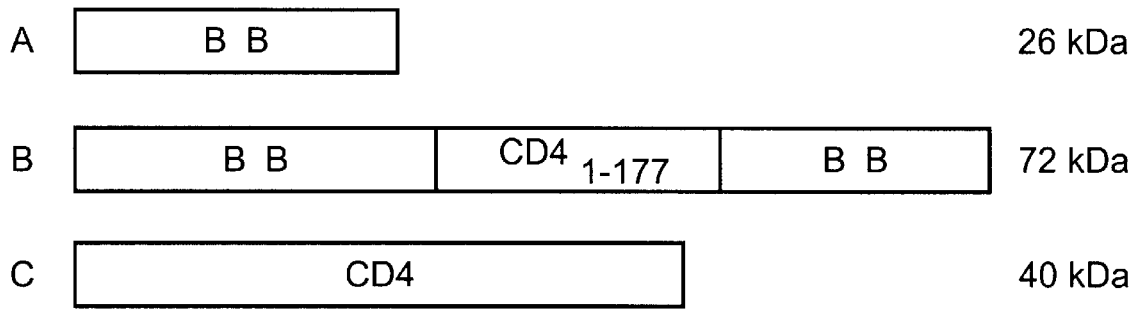
FIG. 4 is a schematic drawing of the proteins encoded by the different plasmid constructs used in the example: row A: pB1B2T, row B: pBB-CD4-BB, row C: the complete extracellular part of the human CD4 receptor (KabiGen AB, Stockholm, Sweden)

Plasmid pB1B2 was digested with endonucleases EcoRI and HindIII to release a 650 bp fragment encoding the serum albumin binding BB domains of streptococcal protein G. This gene fragment was inserted into plasmid pNP-3 previously digested with EcoRI and HindIII. The resulting construction (FIG. 4) designated pEBB-CD4-BB thus encodes a tripartite fusion protein where the CD4 part is flanked by two serum albumin binding regions. *E. coli* RR1 M15 cells harboring the pEBB-CD4-BB plasmid were grown overnight at 30° C. in TSB (Tryptic Soy Broth) containing Ampicillin (100 mg/l). BB-CD4-BB protein was affinity purified from the culture medium using HSA-Sepharose according to standard procedures. Reference CD4 protein containing the complete extracellular region of the human CD4 receptor was obtained from KabiGen (Stockholm, Sweden).

Culture media from an overnight culture of *E. coli* RR1 M15 cells harboring the plasmid pEBB-CD4-BB was passed through an HSA-Sepharose column. Eluted proteins were analyzed by SDS-PAGE and a major band was seen, with an apparent Mr of 73.000, as expected from the deduced amino acid sequence.

Lyophilized BB-CD4-BB protein was dissolved in PBS-buffer and analyzed for gp120 binding activity in a modified competitive ratio immunoassay.

Microtiter plates were coated with mouse monoclonal antibodies (F58/H43, P. A. Broliden et al., 1990, J. of Virology, 54, 936–940) for an HIV gp120 determinant using standard procedures. After washing with PBST-buffer the wells were incubated with gp120 protein in PBS-buffer (L. Lasky et al., 1986, Science 233, 209–212). After rinsing with PBST-buffer, BB-CD4-BB at different concentrations was allowed to compete with labelled CD4-protein (KabiGen AB, Stockholm, Sweden) in binding to the immobilized gp120 protein. After washing the cpm in the wells was determined using standard methods. As negative control BB protein was used and was obtained from cultivation of *E. coli* cells harboring plasmid pB1B2T encoding the BB domain of streptococcal protein G followed by the trpT termination signals (J. Mol. Recognition (1988), 1 (69–74).

Figure 5:
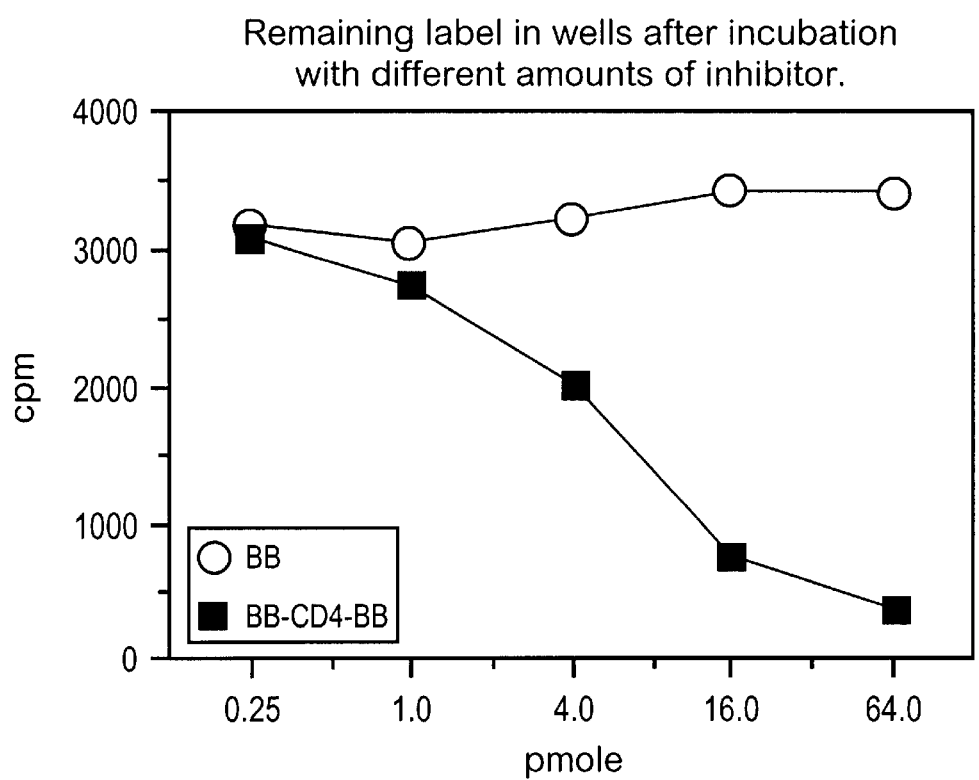
FIG. 5 shows the result from the modified radioimmunoassay for the analysis of the biological activity for the BB-CD4-BB fusion protein.

As shown in FIG. 5 the characteristics of the inhibition obtained for increasing amounts of BB-CD4-BB is significantly different from the control, indicating a true biological activity.

In order to investigate serum half lifes Balb/C mice were injected using a tail vein with labelled proteins BB, BB-CD4-BB and CD4, respectively. At different time points during a 48 hour period blood samples were taken and the cpm per mg plasma determined.

As a reference (100%) value, the cpm per mg at 20 min post injection was used.

Figure 6:
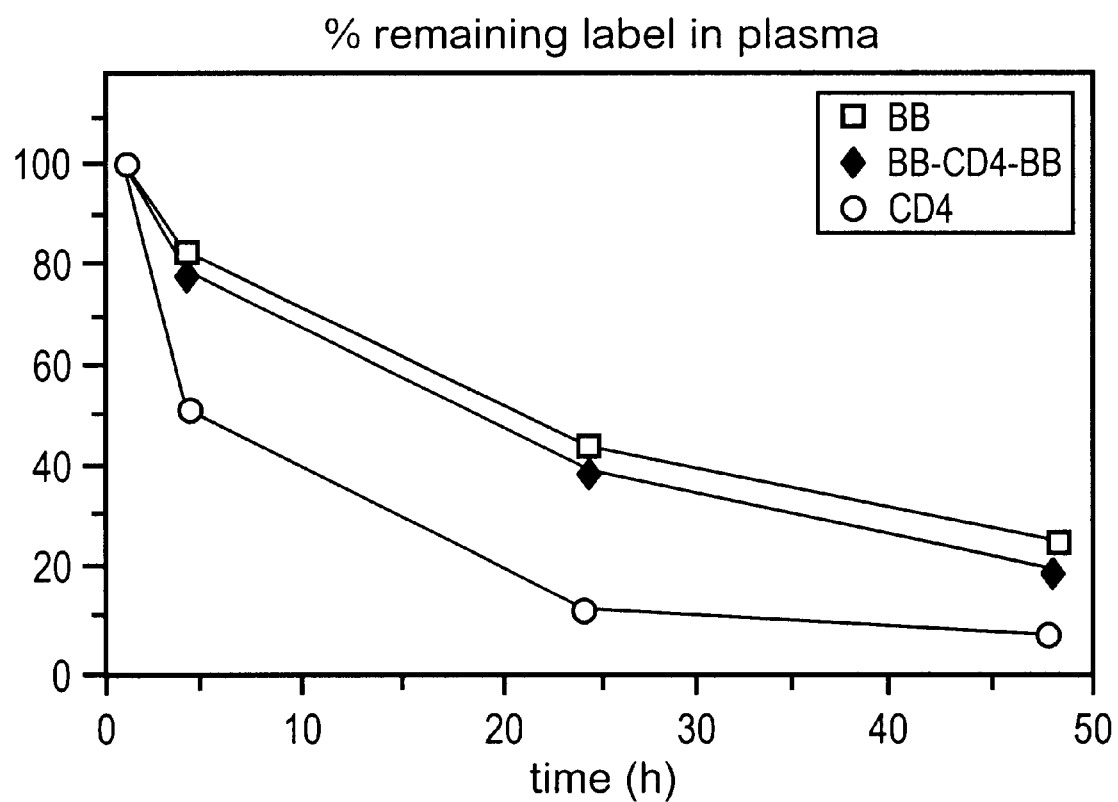
FIG. 6 shows the levels of label remaining in the blood circulation during a 48 hour period in mice injected with $^{125}$I-labelled proteins BB, BB-CD4-BB and CD4. Values are relative to levels observed 20 minutes after injection.

The results shown in FIG. 6 indicate that the strategy to fuse the CD4 molecule to the serum albumin receptor results in an increased serum half-life for this hybrid molecule (BB-CD4-BB) as compared to the unfused counterpart (CD4).

What is claimed is:

1. An improvement in a method of administering a biologically active protein or peptide, wherein the improvement comprises administering a conjugate containing said biologically active protein or peptide and a polypeptide of bacterial origin that binds to a serum albumin protein of mammalian origin, wherein said biologically active protein or peptide containing conjugate exhibits enhanced in vivo half-life relative to a compound consisting of said biologically active protein or peptide.

2. The method of claim 1, wherein said biologically active protein or peptide is a tPA or a hormone.

3. The method of claim 2, wherein said hormone is selected from the group consisting of hGH, IGF-I, IGF-II, TNF, EGF, insulin and relaxin.

4. The method of claim 1, wherein said polypeptide of bacterial origin is obtained from Staphylococcus protein A or Streptococcus protein G.

5. The method of claim 4, wherein said bacterial polypeptide is Streptococcus protein G.

6. The method of claim 4, wherein said bacterial protein is Staphylococcus protein A.

7. The method of claim 1, wherein said conjugate is a recombinant protein.

8. The method of claim 1, wherein said conjugate is administered by injection.

9. The method of claim 1, wherein said administration elicits an immunological response against said biologically active protein or peptide.

* * * * *